United States Patent
Xu et al.

(10) Patent No.: US 7,485,738 B2
(45) Date of Patent: Feb. 3, 2009

(54) METHOD FOR PREPARING HIGH-CONTENT FOOD-GRADE ZEAXANTHIN

(75) Inventors: Xinde Xu, Zhejiang (CN); Lihua Zhang, Zhejiang (CN); Boqiu Chen, Zhejiang (CN); Di Zhou, Zhejiang (CN); Shuangming Ye, Zhejiang (CN); Chiyu Ding, Zhejiang (CN); Hongping Lv, Zhejiang (CN); Bin Shao, Zhejiang (CN)

(73) Assignee: Zhejiang Medicine Co., Ltd., XinChang Pharmaceutical Factory, XinChang County, Shaoxing, Zhejiang (CN)

( * ) Notice: Subject to any disclaimer, the term of this patent is extended or adjusted under 35 U.S.C. 154(b) by 0 days.

(21) Appl. No.: 11/857,248

(22) Filed: Sep. 18, 2007

(65) Prior Publication Data

US 2008/0081932 A1 Apr. 3, 2008

(30) Foreign Application Priority Data

Sep. 28, 2006 (CN) .................. 2006 1 0053642

(51) Int. Cl.
*C07C 51/353* (2006.01)
(52) U.S. Cl. ...................... 554/125; 568/816
(58) Field of Classification Search ................ None
See application file for complete search history.

(56) References Cited

U.S. PATENT DOCUMENTS 6,262,284 B1 * 7/2001 Khachik .............. 554/14

OTHER PUBLICATIONS

Chem Abstr. of CN 1915970.*
Chem Abtsr. of 2004074642.*
Chem Abstr. of CN 1915970, 2007.*
Chem Abtsr. of 2004074642, 2004.*

* cited by examiner

*Primary Examiner*—Deborah D Carr
(74) *Attorney, Agent, or Firm*—Global IP Services; Tianhua Gu

(57) ABSTRACT

This invention has disclosed a method for preparation of food-grade zeaxanthin through chemical isomerizaton reaction from lutein. The technical issues to be solved in this invention are quite low product yield obtained with existing methods, need of purification treatment process, and inadaptability to industrialized production. The technical schemes of this invention are: a. Mix xanthophyll crystal or its fatty acid ester with food-grade glycol or propylene glycol, for full dissolution under 60-90° C. temperature. Add organic alkali into the mixed liquor acquired from step 1, for isomerization reaction to take place under inertial environment. c. Dilute the reaction solution gained from step b with the mixed solution of deionized water and ethanol, and separate the obtained crystal with conventional separating method. d. Vacuum dries the acquired crystal from step c, to get the zeaxanthin crystal. Glycol or propylene glycol is used in this invention for isomerization reaction under inertial environment after it has fully dissolved raw material under proper temperature. The product yield is reachable to more than 60%, very adaptable to industrialized product, without the need for further purification treatment.

8 Claims, No Drawings

METHOD FOR PREPARING HIGH-CONTENT FOOD-GRADE ZEAXANTHIN

CROSS REFERENCE TO RELATED PATENT APPLICATION

This patent application claims the priority of the Chinese patent application No. 200610053642.3 with filing date of Sep. 28, 2006.

FIELD OF THE INVENTION

This invention belongs to biochemical domain, and specifically speaking it is a method for preparing high-content food-grade zeaxanthin by making use of naturally extracted xanthophyll through chemical transposition.

BACKGROUND OF THE INVENTION

As known to all, carotenoid is a kind of very important substance. Carotenoid is often composed through coupling of molecules of five carbon atoms, namely isoprene, and there are multiple unsaturated bonds in the molecular structure. The existence of these conjugated double bonds has endowed carotenoid with related color and some important physiological functions. While based on whether or not oxygen exists in the molecular structure, carotenoid can be further divided into two types, carotenes and xanthophyll, respectively, the former including α-, β-, γ-carotenes, and lycopene, etc, while the latter covers lutein, zeaxanthin, astaxanthin, and canthaxanthin, etc. These carotenoids are all biochemically and commercially quite important, and all have corresponding important physiological functions. The lutein and zeaxanthin of them have aroused increasing recognition from people in recent years, and new progresses have been made continually on research and product development related in this area.

The structural formulas of lutein and zeaxanthin are respectively as follows. They are isomers and the only difference between the two structural formulas is the positions of double bonds on one (instead of two) end ring. The positions of double bonds on two end rings for the former are symmetrical, while those for the latter are asymmetrical. The entire linear chain part for each molecule of lutein and zeaxanthin is a conjugated structure, namely, provided with alternate double bonds and single bond. In the molecule of zeaxanthin, the conjugated structure extends to the first bond on the two end rings, while the conjugated degree for lutein is even lower, as the correct arrangement of complete conjugated structure has not yet been formed for double bonds on one of its end rings. This is the discrepancy in molecular structure that has caused certain difference in the functions of lutein and zeaxanthin.

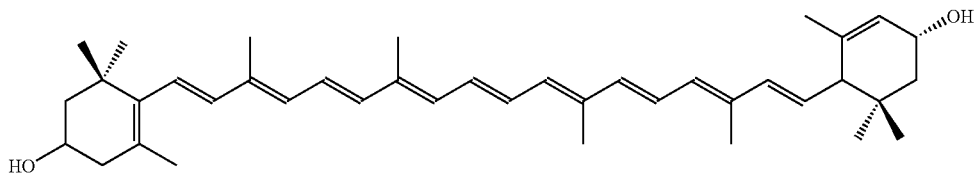

Lutein (Molecular Formula: $C_{40}H_{56}O_2$ Molecular Weight: 568.85)

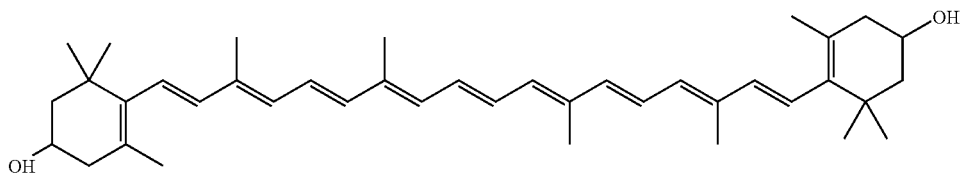

Zeaxanthin (Molecular Formula: $C_{40}H_{56}O_2$ Molecular Weight: 568.85)

As natural pigment matters lutein and zeaxanthin have a very wide distribution in natural world. They mainly exist in higher plants, alga, fishes, shells, and bacteria, and they always exist inside organisms in the form of esters. In these matters, marigold is a good source of lutein and zeaxanthin, and there is often about 2 g xanthophylls in 100 g marigold fresh flowers, mainly lutein wherein, accounting for more than 90%, while the rest are zeaxanthin and a few other carotenoids. The same as in marigold, among sources from other higher plants and alga, lutein has accounted a larger proportion relative to zeaxanthin, while the amount of zeaxanthin is larger than that of lutein in corn.

Additionally, it has also indicated in molecular structure that stereo isomerism exists in lutein and zeaxanthin, and the structure of stereo isomerism varies along with different sources, as in plant raw material (3R,3'R,6'R)-lutein or (3R,3'R)-zeaxanthin are the main forms, but in animal sources such as fishes and shells, lutein exists in the (3R,3'R,6'R)—, (3R,3'R,6'S)—, and (3R,3'S,6'S)— forms, while zeaxanthin exists in the (3R,3'S)— and (3S,3'S)— forms.

As a kind of carotenoid, lutein and zeaxanthin are initially and now still used as a pigment, such as used in the pigmentation of egg yolk, the out skins of poultry (such as skin, leg, and beak) and hypodermal fat, muscle, as well as the outer skins of fishes and shells (skin, scale, and shell). Also it has recently begun to use lutein and zeaxanthin as a functional food colorant. However, as mentioned afore, as there is one extra conjugated double bond in the molecular structure of zeaxanthin than that of lutein, zeaxanthin can show stronger golden yellow color and more lasting color than lutein, and on this account, zeaxanthin is preferred for use under many conditions.

Besides, lutein and zeaxanthin are the only two carotenoids existing in the retina of human body, and they are very important for curing and preventing age-related macular degeneration (ARMD) disease, able to effective protect eyes from suffering ARMD and blindness therefrom. Since zeaxanthin is fully conjugated, it is able to certain degree to provide better protective function for trauma arising from resistance to luminous energy.

In fact, some researches in the mid and late stages of the 80s have also proved that zeaxanthin exists mainly in the subzone at the positive macular center of human eyes, and the amount of zeaxanthin would gradually reduce deviating concentrically from the sunken part and approaching the outer macular circumference, while that of lutein will gradually increase alongside. In the macular periphery, lutein is the main yellow coloring matter.

As mentioned afore, lutein and zeaxanthin is a kind of important colorant and component with unique physiological activity. However, as animal bodies themselves are not able to synthesize carotenoid, they must digest lutein and zeaxanthin from plant sources. There is relatively abundant lutein in the source of plants, and it has been achieved to extract lutein from plants on a large scale, while it is evidently unrealistic to extract zeaxanthin which has the same and even superior efficacy as lutein from plants. Thus, it is necessary to get high-content edible zeaxanthin suitable to human beings through other approaches.

Talking about existing techniques, preparation of zeaxanthin can be basically divided into 3 types—fermentation method, complete chemical synthesis method, and transposition from lutein. The microorganisms used for fermentation method are mainly cells of Flavobacterium. The defect with zeaxanthin produced by fermentation method is the output of most microorganisms is rather low, and sometimes there is a high content of needless or possibly harmful S—S configuration and meso isomers in the fermented products. Moreover, fermented products shall pass through a rather tanglesome follow-up extraction process. The severe disadvantage with complete chemical synthesis method is that they usually need many reaction steps, with a low yield of final products, and during chemical synthesis course, it may generate more needless S—S and S—R stereoisomers of zeaxanthin, in addition to various transformed and degraded products. From a comparison with the two abovementioned methods, it may be a promising method to produce zeaxanthin with lutein transposition method, as only one step reaction is involved in this process. Under the circumstance when reaction condition is well controlled, the product yield will be rather high, and only one kind of R—R isomer of zeaxanthin may exist in the product, with comparatively higher physiological activity.

The patent of CN1082507C has disclosed a method for making zeaxanthin through chemical transposition using lutein as raw material, where mainly the mixture of dimethyl sulfoxide or with saturated alkane and/or arene organic solvent is used as solvent, and hydroxide of alkali metals is used as catalyst to produce zeaxanthin through transposition of lutein. However, in this process, the dosage of alkali is quite great, reaching 250-500 times (mol ratio) that of the lutein raw material. Under the effect of strong alkali at this high concentration, high temperature (80-100° C.) and long duration (reaction time reaching tens of hours), it may cause quite a large part of lutein and the generated zeaxanthin to be degraded or carbonized, though the proportion of zeaxanthin against total carotenoid in the final product after refined crystal with $CH_2Cl_2/CH_3OH$ can reach 90% or so, the yield of products is quite low (The repeated tests have indicated that the product yield by this method is less than 30%), and therefore it is not suitable for industrialized production. When catalysts for phase transfer are used, the treatment process of extraction, column chromatography or re-crystallized purification is specially required, to ensure the product purity. Moreover, hexane, heptane, dichloromethane, methanol, and other organic solvents have been used in reaction process, while it is evidently improper to produce food-grade or medicine-grade zeaxanthin using these toxic solvents.

SUMMARY OF THE INVENTION

Technical issue to be solved by this invention is to overcome the abovementioned defects existing techniques, to provide a preparation method with high product yield, free from re-crystallization of product and purification treatment for column separation, and applicable to industrialized production of food-grade zeaxanthin.

For this purpose, the following technical scheme is adopted in this invention—preparation method for high-content food-grade zeaxanthin, and its steps are given as follows: a. Mix the crystals of xanthophyll or its fatty acid ester with food-grade glycol or propylene glycol, and fully dissolve it under 60-90° C. temperature. b. Instill organic strong base solution to the mixture gained from step a, and the isomerization reaction to take place under inertial environment. c. Dilute the reaction substance acquired from step b with a mixture of deionized water and ethanol, and separate the obtained crystals with conventional separation method. d. Vacuum dry the crystals obtained from step c, namely to get the zeaxanthin crystals. This invention is a method for producing zeaxanthin through isomerization reaction, with organic strong base as catalyst in the food-grade glycol or propylene glycol solvent by making use of naturally extracted lutein fatty acid ester or lutein crystal as raw material. Glycol or propylene glycol has better dissolvability to xanthophyll fatty acid ester or xanthophyll crystal than ethanol, and able to fully dissolve the raw material under 60-90° C. temperature, which is very beneficial to the isomerization reaction of this invention. The content of total carotenoid in the product gained through this method is more than 80% and the product yield can reach 60%. The zeaxanthin accounts for as high as 90% or so in the total carotenoid content. There is no need for re-crystallization and purification treatment for column separation, which has simplified process. Moreover, it is mainly an R—R configuration with rather high biological activity. The proportion of lutein in total carotenoid is between 5-15%. No toxic and harmful residue of organic solvents has been detected in products, proper to be used as food additive or medicine. In order to protect raw material xanthophylls and the generated zeaxanthin from being oxidized, an inertial environment shall be created during reaction process, namely to fill nitrogen into the reaction system as protection. The duration of reaction in this invention is short as 3-15 hours generally. During crystal separation, water and ethanol can be continuously used for washing, until the crystal shows rather bright and beautiful saffron color or tangerine color, ready to get zeaxanthin crystals after vacuum drying. Ultraviolet visible light spectrophotometric method and high performance liquid chromatographic method are used to measure the content of total carotenoid and the proportion of zeaxanthin and lutein in total carotenoid in the products, respectively.

As a further technical scheme of this invention, the temperature for isomerization reaction is 60-120° C. The isomerization reaction of this invention is to be performed as much as possible under a temperature not exceeding 120° C., and the preferred temperature for this invention is 80-95° C., to avoid as much as possible the generation of byproducts and degradation of zeaxanthin. A too high reaction temperature will accelerate oxidation of reactant and product, to lower the yield of final products, while a too low reaction temperature would lead to under-reaction and prolonged reaction duration, which is also not helpful to increase in product yield.

In the described preparation method of high-content food-grade zeaxanthin, the preferred dissolving temperature for xanthophyll crystal or its fatty acid ester and food-grade alcohols is 70-80° C., to avoid as much as possible the occurrence of degradation.

In the described preparation method of high-content food-grade zeaxanthin, the organic alkali is sodium methoxide, sodium ethoxide, sodium tertiary butyl alcohol, sodium dimethyl sulfoxide, or potassium methoxide, and potassium ethoxide, and its dosage level is a molar weight 1-15 times that of the raw material, preferred a molar weight by 4-10 times. The catalyzing effect of organic alkali is superior to hydroxide of alkali metals, and its dosage is evidently less than that of the hydroxide of alkali metals. The concentration of organic alkali is low, the lowest reachable to 1.50 mol/L. A too large amount of catalyst may prompt xanthophyll in raw material and zeaxanthin in product to be carbonized, leading to a low yield, while too small amount of catalyst may be disadvantaged to reaction and cause reaction duration to be prolonged.

In the described preparation method of high-content food-grade zeaxanthin, the dosage of glycol or propylene glycol is a volume proportion 2-40 times that of the raw material, the preferred being 5-20 times.

In the described preparation method of high-content food-grade zeaxanthin, the used raw material xanthophyll fatty acid ester or xanthophyll crystal is sourced from marigold, the former refined from oleoresin of marigold, wherein the content of total carotenoid accounting for more than 60%, and the latter being the crystal obtained after saponification of marigold oleoresin. Decrease in proportion of lutein in raw material and increase in proportion of zeaxanthin is beneficial to the quality of final products in this method.

Glycol or propylene glycol used in this invention is to be performed with isomerization reaction under inertial environment after it has fully dissolved raw material under proper temperature. The acquired product zeaxanthin crystal accounts for about 90% of the total carotenoid content, and the product yield can reach more than 60%, very adaptable to industrialized production, without any further need for re-crystallization, column separation, and other purification procedures, with simplified process. The concentration of organic alkali is low, with the lowest reachable to 1.50 mol/L, and the dosage of alkali is low. The reaction duration is short, generally 3-15 hours. No residue of organic solvents which has been limited for use in human food exists in products, able to be used as food additive or medicine.

This invention is further descried with following examples. However this invention is not to be limited by the listed examples.

DETAIL DESCRIPTION OF THE INVENTION

EXAMPLE 1

Weigh 30 g xanthophyll crystal from saponification of marigold oleoresin (wherein the total carotenoid is 88.5% and the proportions of lutein and zeaxanthin account for 92% and 7% of total carotenoid, respectively, the rest being a few other carotenoids). Mix with 540 ml glycol and stir and dissolve for 1.0 hr under 80° C. Heat up the mixture to 90° C. after dissolution is completed, and instill 40 g 6.85 mol/L sodium methoxide solution, and addition of alkali catalyst is to be completed within 45 min. Reaction is to take place at this temperature, and the lutein and zeaxanthin in the reaction solution are to be sampled at an interval of 0.5 hr after reaction for 4.0 hr and analyzed with high performance liquid chromatographic method for their proportions, to get a measurement of 89.7% proportion of zeaxanthin of total carotenoid in the reaction liquid after 8.5 hr. Drop the temperature of reaction mixture to 70° C., and add a mixture composed of 1000 ml deionized water and 600 ml food-grade ethanol under the stirring condition to dilute the reaction substance. While separating crystals from the diluent mixed solution with centrifugal method, a mixture of water and ethanol is used for spraying rinse, until the washed out liquid is nearly colorless. 21.3 g tangerine colored crystal can be obtained for the final filtrated matter through vacuum drying. Analyzed by ultraviolet visible light spectrophotometric method, the total carotenoid content in this crystal is 85.7%. The yield of total carotenoid is 68.6%. Analyzed with high performance liquid chromatographic method, the zeaxanthin wherein account for 91.2% of total carotenoid and the lutein occupies 6.1% of total carotenoid.

No toxic organic solvent is contained in the products, suitable to be used in the forms of nutrition extender and food additive. The application form of this crystal can be oil suspension (mixed and emulsified with plant oil), granule beads (microcapsule condensed through spray condensation granule beads technology), and dry powder (microcapsule through spray-drying), etc.

Operating conditions and product characters in this example are listed in Table 1.

EXAMPLE 2

Weigh 40 g xanthophyll fatty acid ester refined from marigold oleoresin (wherein the carotenoid fatty acid ester content of total carotenoid is 72.5%, and the proportions of lutein and zeaxanthin in total carotenoid are 91.6% and 6.8%, respectively, the rest being a few other carotenoids). Fully mix xanthophyll fatty acid ester with 470 ml propylene glycol and dissolve the mixture under 70° C. Heat up to 85° C. after dissolution is completed. Add 110 g 2.92 mol/L sodium tertiary butyl alcohol solution drop by drop, and it is determined after reaction standing for 14.5 hr with high performance liquid chromatographic method that zeaxanthin wherein accounts for an 84.6% proportion of the total carotenoid. Cool down to 70° C. and add a mixed liquid composed of 1000 ml deionized water and 600 ml food-grade ethanol to dilute the reaction liquor. Extract and filter out the crystals from separation, with a mixture of water and ethanol for washing during the extracting and filtering process, until the washed out liquid is nearly colorless. 10.3 g saffron colored crystal is gained from the filtrated insoluble substance after vacuum drying. Analyzed with ultraviolet visible light spectrophotometric method, the total carotenoid content in the crystal is 81.3%, while the yield of total carotenoid is 54.0%. Through HPLC analysis, zeaxanthin in the product accounts for 85.2% of the total carotenoid, and the lutein occupies 11.3% of the total carotenoid, both in dissociative forms.

Operating conditions and product characters in this Example are listed in Table 1.

EXAMPLES 3-4

Implementation processes for Examples 3-4 are similar to those of Examples 1-2, and the analytical results for their main technical parameters and some product characters are listed in Table 1.

TABLE 1

Analysis of Main Technical Parameters and Some Product Characters in Examples 1-4

| Item | Example 1 | Example 2 | Example 3 | Example 4 |
| --- | --- | --- | --- | --- |
| Type of Raw Materials | Xanthophyll Crystal | Xanthophyll Fatty Acid Ester | Xanthophyll Crystal | Xanthophyll Fatty Acid Ester |
| Quantity of Raw Material | 30 g | 40 g | 30 g | 40 g |
| Type of Solvent | Glycol | Propylene Glycol | Propylene Glycol | Glycol + Propylene Glycol (1:1) |
| Quantity of Solvent | 540 ml | 470 ml | 450 ml | 400 ml |
| Type of Catalyst | 6.85 mol/L Sodium Methoxide Solution | 2.92 mol/L Sodium Tertiary Butyl Alcohol Solution | 1.96 mol/L Sodium Dimethyl Sulfoxide Solution | 5.15 mol/L Sodium Ethoxide Solution |
| Quantity of Catalyst | 40 g | 110 g | 150 g | 83 g |
| Reaction Temperature | 90° C. | 85° C. | 80° C. | 90° C. |
| Reaction Duration | 8.5 hr | 14.5 hr | 6.0 hr | 12.0 hr |
| Separating Method | Centrifugal | Extraction and Filtration | Extraction and Filtration | Centrifugal |
| Quantity of Product | 21.3 g | 10.3 g | 17.3 g | 9.7 g |
| Total Carotenoid Content in Product | 85.7% | 81.3% | 88.4% | 83.5% |
| Proportion of Zeaxanthin of Total Carotenoid | 91.2% | 85.2% | 92.3% | 91.8% |
| Proportion of Lutein of Total Carotenoid | 6.1% | 11.3% | 6.1% | 7.0% |
| Yield of Total Carotenoid | 68.8% | 54.0% | 57.6% | 51.7% |

What is claimed is:

1. A method for preparing high-content food-grade zeaxanthin comprising following steps:
   a. mixing crystals of xanthophyll or its fatty acid ester with food-grade glycol or propylene glycol under 60-90° C. temperature until the crystals of xanthophyll or its fatty acid ester is full dissolved;
   b. dripping organic strong base solution into the mixed liquor gained from step a then put them in inertial environment to take isomerization reaction under 60-120° C.;
   c. diluting the reaction solution acquired from step b with a mixture of deionized water and ethanol, then separating obtained crystals by conventional separation method;
   d. vacuum dry the crystals gained from step c, to get crystals of zeaxanthin.

2. The method for preparing high-content food-grade zeaxanthin according to claim 1, wherein the temperature for the isomerization reaction is 80-95° C.

3. The method for preparing high-content food-grade zeaxanthin according to claim 2, wherein the temperature for dissolution of crystal of xanthophyll or its fatty acid ester and food-grade alcohols is 70-80° C.

4. The method for preparing high-content food-grade zeaxanthin according to claim 3, wherein the organic strong base is sodium methoxide, sodium ethoxide, sodium tertiary butyl alcohol, sodium dimethyl sulfoxide, potassium methoxide, or potassium ethoxide, molar weight of the organic strong base is 1-15 times of the molar weight of the crystals of xanthophyll or its fatty acid ester.

5. The method for preparing high-content food-grade zeaxanthin according to claim 4, wherein the molar weight of the organic strong base is 4-10 times that of the crystals of the xanthophyll or its fatty acid ester.

6. The method for preparing high-content food-grade zeaxanthin according to claim 5, wherein the glycol or propylene glycol as a volume 2-40 times that of the crystals of xanthophyll or its fatty acid ester.

7. The method for preparing high-content food-grade zeaxanthin according to claim 6, wherein the glycol or propylene glycol as a volume 5-20 times that of the crystals of xanthophyll or its fatty acid ester.

8. The method for preparing high-content food-grade zeaxanthin according to claim 7, wherein the xanthophyll fatty acid ester or xanthophyll crystal is derived from marigold, the former being refined from oleoresin of marigold containing more than 60% of total carotenoid ester content, and the latter is the crystal derived from oleoresin of marigold through saponification treatment.

* * * * *